(12) United States Patent
Semmlow

(10) Patent No.: US 10,194,867 B1
(45) Date of Patent: Feb. 5, 2019

(54) SYSTEM AND MEANS FOR ESTIMATING THE SIGNAL-TO-NOISE RATIO OF ACQUIRED SIGNALS

(71) Applicant: John Leonard Semmlow, New Brunswick, NJ (US)

(72) Inventor: John Leonard Semmlow, New Brunswick, NJ (US)

( * ) Notice: Subject to any disclaimer, the term of this patent is extended or adjusted under 35 U.S.C. 154(b) by 0 days.

(21) Appl. No.: 15/805,177

(22) Filed: Nov. 7, 2017

(51) Int. Cl.
*A61B 5/02* (2006.01)
*A61B 5/00* (2006.01)
*A61B 7/02* (2006.01)

(52) U.S. Cl.
CPC .......... *A61B 5/7203* (2013.01); *A61B 5/7225* (2013.01); *A61B 5/7246* (2013.01); *A61B 7/02* (2013.01)

(58) Field of Classification Search
CPC ... A61B 5/7203; A61B 5/7225; A61B 5/7246; A61B 7/02
See application file for complete search history.

(56) References Cited

U.S. PATENT DOCUMENTS

| | | |
|---|---|---|
| 5,036,857 A | 8/1991 | Semmlow et al. |
| 5,109,863 A | 5/1992 | Semmlow et al. |
| 9,226,726 B1 | 1/2016 | Semmlow |
| 9,320,489 B1 | 4/2016 | Semmlow |

OTHER PUBLICATIONS

Wang, P., Tie, B., Welkowitz, W., Semmlow, J., and Kostis, J. "Modeling Sound Generation in Stenosed Coronary Arteries" Biomedical Engineering, vol. 35, No. 3, pp. 367-374, Mar. 2007.
Semmlow J.L., Welkowitz W., Kostis J., and Mackenzie J.W., "Coronary artery disease-correlates between diastolic auditory characteristic and coronary artery stenosis," IEEE Trans. Biomed. Eng., vol. BME-30, pp. 136-139, 1983.
Semmlow, J., and Rahalkar, K., "Acoustic detection of coronary artery disease," Annual Rev of Biomed, Engr. vol. 9: pp. 449-469, Apr. 2007.
Vermarien, H,. Vollenjoven, E. 1984. The recording of heart vibrations: a problem of vibration measurement on soft tissue. Med. Biol. Eng. Comput. vol. 22, pp. 168-178.
Padmanahban, V., and Semmlow J., Accelerometer type cardiac transducer for detection of low-level heart sounds. IEEE Trans. Biomed Engr. vol. BME-40, pp. 21-28,1993.
Akay, Y.M., Akay, M.A., Welkowitz, W., Semmlow, J.L., and Kostis, J.B., "Noninvasive detection of coronary artery disease: A comparative study of signal processing methods," IEEE Trans. Biomed. Engr. vol. 40, pp. 571-578, 1993.

*Primary Examiner* — Lindsey G Wehrheim
(74) *Attorney, Agent, or Firm* — Marc D. Lowy

(57) ABSTRACT

The present invention is an apparatus for detection of high-frequency heart sounds for diagnosing heart diseases. One embodiment utilizes an accelerometer-based detector that presents a light load to the chest, is sensitive to the desired high frequency range, and provides a quantitative measurement of the quality of the acquired signal. Two piezoelectric sensors are positioned so that they respond to the same mechanical energy and will produce identical electrical signals in the absence of noise. Through signal processing means the two signals can provide an estimate of the signal-to-noise ratio of the acquired signal. The two signals can also be combined to further improve the signal-to-noise ratio.

18 Claims, 7 Drawing Sheets

SYSTEM AND MEANS FOR ESTIMATING THE SIGNAL-TO-NOISE RATIO OF ACQUIRED SIGNALS

CROSS REFERENCE TO RELATED APPLICATION(S)

Not Applicable.

FIELD OF INVENTION

The present invention relates to a method and system for noninvasive detection of the early stages of coronary artery disease based on identification of high-frequency heart sounds from the chest, and more particularly, a method and system for assessment of the quality of acquired heart sound signals.

BACKGROUND

There are devices presently available to detect acoustic signals from the chest each having its own advantages and disadvantages as described in the review by Semmlow and Rahalkar. The motivation for most of these devices is the detection of sound signatures associated with coronary artery disease as originally described by Semmlow el al. in 1983. Coronary artery disease results from occlusions or blockages of the coronary arteries which supply blood to the heart. Such blockages will produce turbulent blood flow including an auditory correlate. Theoretical studies by Wang et al indicate that said auditory correlates will be at relatively high frequencies: above 200 Hz and as high as 1 kHz. Such sounds are generally too faint and at too high a frequency to be heard through a traditional stethoscope, although murmurs associated with coronary artery disease have occasionally been reported. Acoustic detection of the sounds produced by blood flowing through partially occluded coronary arteries would thereby enable the noninvasive detection of this major disease. An accelerometer-based sensor described by Padmanahban et al. and in U.S. Pat. Nos. 5,036,857 and 5,109,863 has produced signals that were moderately successful in detecting coronary artery disease as shown by Akay et al. Semmlow (U.S. Pat. Nos. 9,226,726 and 9,320,489) describes a similar sensor and system for detecting coronary artery disease noninvasively based on sounds detected from the chest.

The quality of the signals acquired from the chest has a direct impact on the reliability of the diagnosis information derived from that signal. The quality of the signal produced by a cardiac microphone will also depend on microphone position and attachment to the chest along with patient factors such as body weight. Hence the quality of signals produced by any detector will vary from patient-to-patient and even measurement-to-measurement. There is therefore a clear need for a detector which provides quantitative information on the quality of the acquired signal over the range of desired frequencies. The present invention accomplishes these objectives.

Semmlow (U.S. Pat. No. 9,226,726) describes a method based on correlation for determining the signal-to-noise ratio (SNR) given two copies of a signal and associated noise. The present invention is an improved method for evaluating SNR from two signal copies based only on algebraic analysis. This method may be faster to implement on a computer and can provide a more accurate estimate of SNR. It is more robust to imbalances in the two signals and to differences in the noise components of the two signals. The present invention also produces an estimate of both the signal and noise components in addition to the SNR.

SUMMARY

The present invention is a method and system for monitoring and recording heart sounds from the chest and for providing a quantitative assessment of the quality of the heart sound signals so acquired.

In one embodiment of this invention, two signals are produced by two identical sensors comprising the accelerometer-based detector. These signals are amplified, filtered, and converted to a digital signal via an analog to digital converter. The two digital signals are compared using a unique signal processing algorithm to produce an estimate of the Signal-to-Noise Ratio (SNR) of the acquired signals. Signal processing means are provided that first compensate for unequal time shifts and unequal gains in the two signal channels. The signal processing algorithm is applied to the two balanced signals and provides an estimate of the underlying signal and noise components of the detector signal. The ratio of these two components provides the SNR of the acquired signal that can be given in decibels (dB).

In another aspect of this invention, the signals are first band-limited to narrow frequency ranges before the signal processing analysis so that said algorithm provides the SNR as a function of frequency. The two signals are also combined through averaging to produce a single signal with improved SNR.

Other features and advantages of the present invention will become apparent from the following more detailed description, taken in conjunction with the accompanying drawings, which illustrate, by way of example, the principles of the invention 10.

BRIEF DESCRIPTION OF THE DRAWING(S)

The foregoing Summary as well as the following detailed description will be readily understood in conjunction with the appended drawings which illustrate embodiments of the invention. In the drawings.

DETAILED DESCRIPTION OF ILLUSTRATIVE EMBODIMENT(S)

Figure 1:
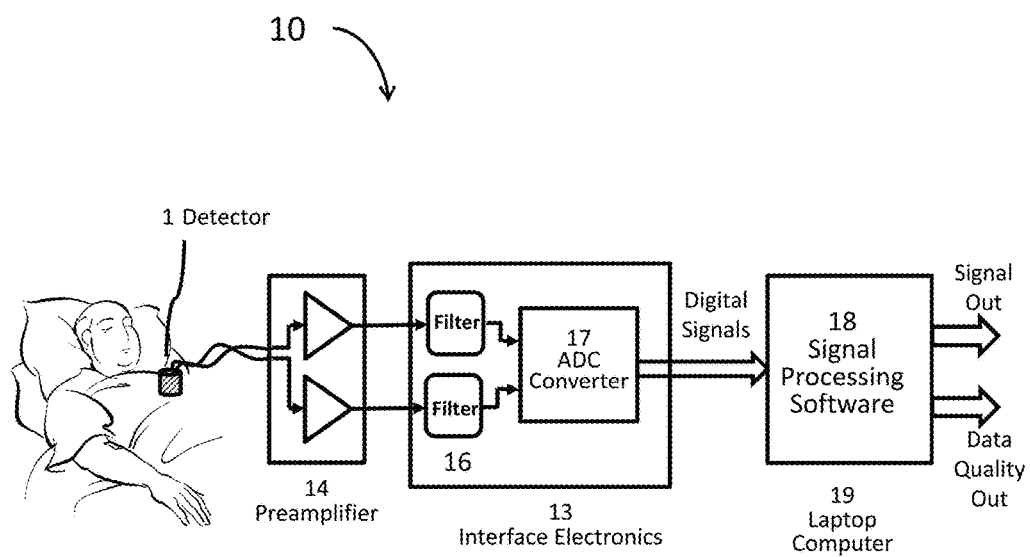
FIG. 1 is a schematic of the overall system illustrating one embodiment of a signal system for acquisition and processing of cardiac acoustic signals.

In FIG. 1 is illustrated a schematic of the overall system including the accelerometer detector 1, preamplifier unit 14, interface electronics unit 13, and computing unit 19 containing signal processing software 18.

The preamplifier unit 14, takes the differential output signals from the accelerometer detector 1 and amplifies them differentially to produce the two resultant signals. The preamplifier unit 14 is constructed from standard low-noise instrumentation amplifiers well-known in the art. The interface electronics unit 13, receives the two signals from the output of the preamplifier unit 14. The two signals are then sent to anti-aliasing filters 16. In the final stage of the interface electronics 13, the two filtered signals are sent to a standard analog-to-digital converter (ADC) 17, preferably having a 16-bit or better conversion accuracy. The ADC 17 generates two digital signals and sends them to the computing unit 19. In one embodiment of the invention 10, a standard laptop computer could be used for the computing unit 19. However, in alternative embodiments, a specially designed computer (not shown) using a dedicated microprocessor could be used to perform these operations. In still another embodiment, a tablet computer (not shown) or even a mobile telephone (not shown) could be used to implement the signal processing software 18.

Figure 2:
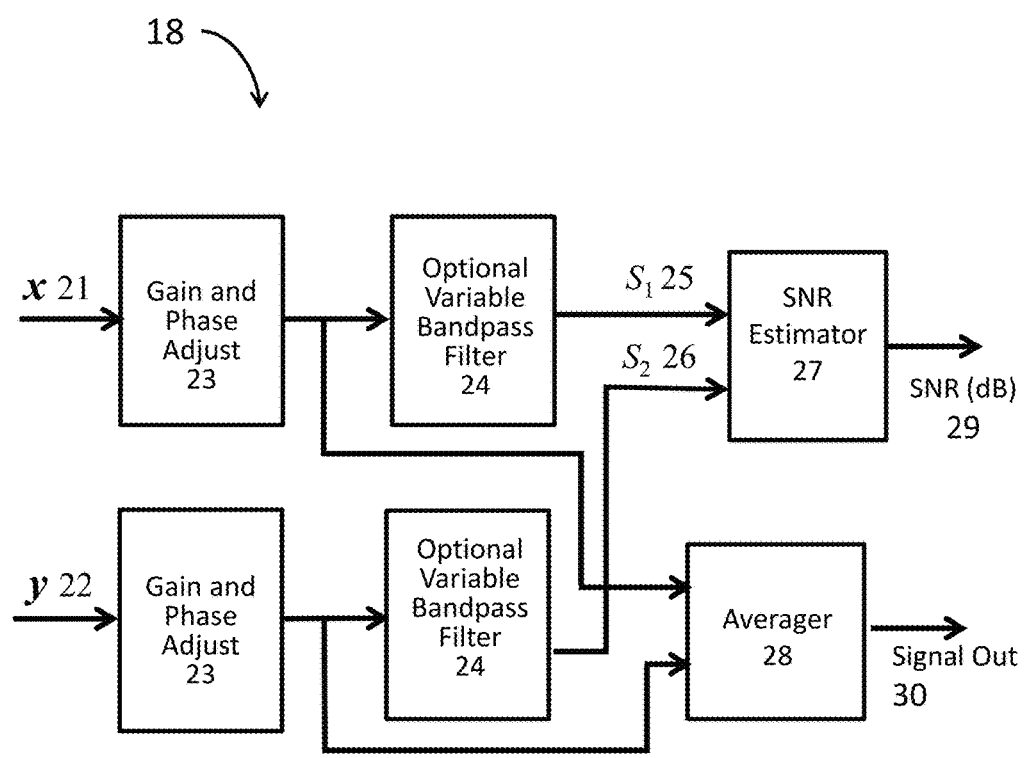
FIG. 2 is a block diagram illustrating one embodiment of the signal processing software.

In FIG. 2 is illustrated a block diagram of one embodiment of the signal processing software 18. The invention 10 uses two copies of the same acoustic signal, each containing its associated noise. Such signals could come for a dual-sensor microphone as described in U.S. Pat. No. 9,226,726 and U.S. Pat. No. 9,320,489. The signal processing software takes the two input signals, x 21 and y 22 from the ADC Converter 17 and applies a gain and phase adjust operation 23 to make their RMS values equivalent by scaling up signal y 22 by a value equal to $x_{rms}/y_{rms}$. Input signal y is then also shifted in the Gain and Phase Adjust operation 23 to give the best alignment between the two signals. To determine the shift values a cross-correlation operation is performed between the two signals:

$$r_{xy}(\tau) = \Sigma x(y-\tau) \qquad \text{Equation 1}$$

The $\tau$ that corresponds to the maximum $r_{xy}$, is used to shift signal y 22. The shifted and balanced signals are then passed to optional variable bandpass filters 24 and to signal averager 28. Signals from the variable bandpass filters 24 are sent to the SNR estimator 27. In other embodiments, the bandpass filters are not used and the adjusted signals are sent directly to SNR estimator 27. The averager 28 combines the two balanced and shifted input signals through standard algebraic averaging to produce a single signal 30 with improved SNR. This signal would be used by subsequent signal processing software in a system for the identification of auditory correlates of coronary artery disease. The SNR estimator 27 receives signals $S_1$ 25 and $S_2$ 26 and uses a novel algorithm that estimates (in decibels) the SNR 29 as explained below.

Figure 3:
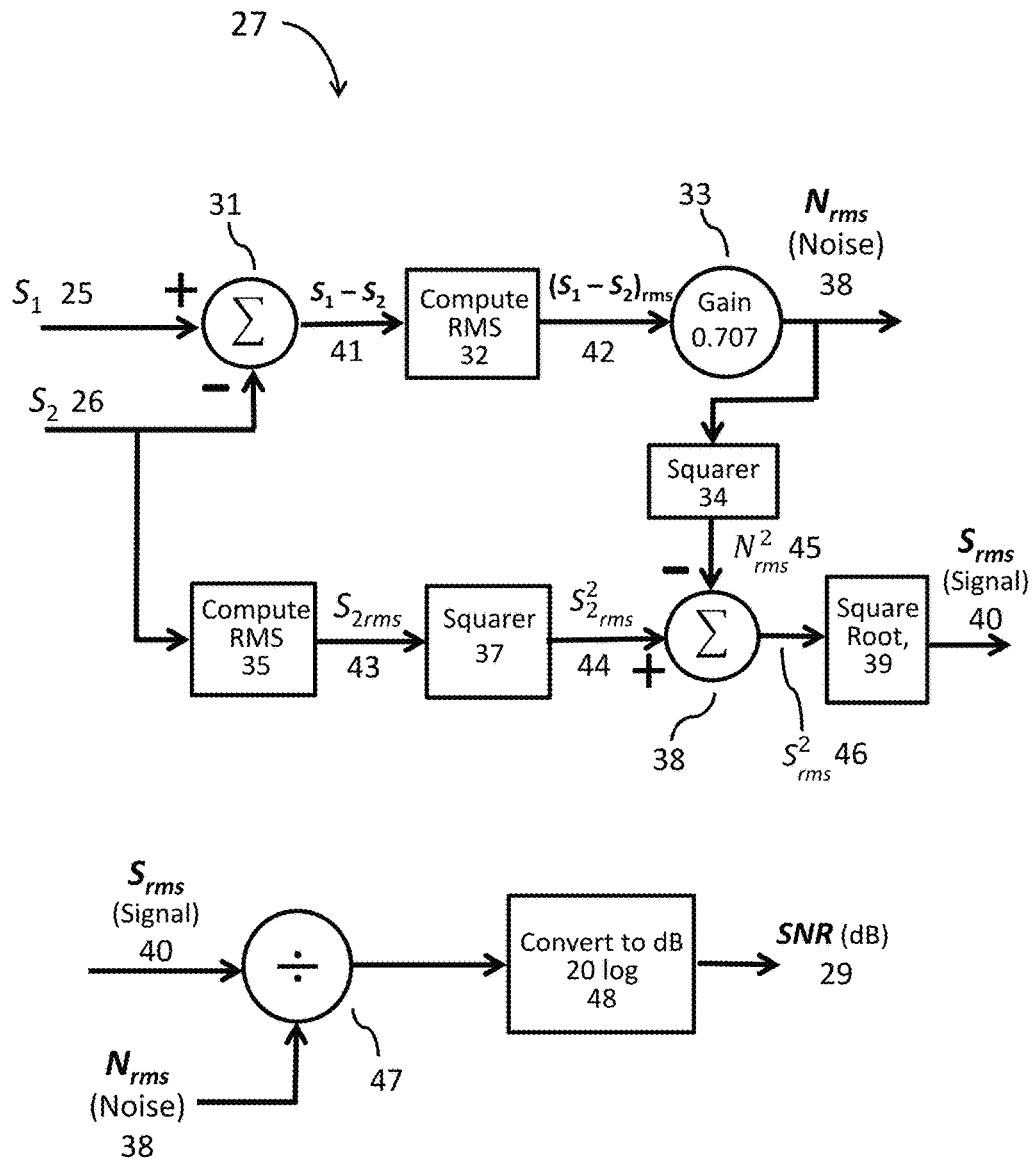
FIG. 3 is a block diagram of the algorithm for computing the estimated SNR using the signal processing software operations shown in FIG. 2.

Referring to FIG. 3, a computer algorithm is applied to input signals $S_1$ 25 and $S_2$ 26 in SNR Estimator 27 to estimate the SNR. The SNR Estimator 27 is based on the fact that each of the two input signals, $S_1$ 25 and $S_2$ 26, consists of the desired underlying signal, S, plus additive sensor noise:

$$S_1 = S + N_1 \qquad \text{Equation 2}$$

$$S_2 = S + N_2 \qquad \text{Equation 3}$$

where $S_1$ 25, and $S_2$ 26 are the input signals to the SNR estimator, 27. $N_1$ and $N_2$ are the noise contained in the two input signals, 25 and 26, and S is the underlying signal without the noise. To estimate the SNR of the input signals, $S_1$ 25 and $S_2$ 26, it is necessary to estimate S, $N_1$, and $N_2$.

Subtracting the two measured signals, $S_1$ 25 and $S_2$ 26, in Subtractor 31 should eliminate the common underlying signal component, S, in the subtracted signal 41. The root-mean-squared (RMS) value of the subtracted input signal, $(S_1-S_2)_{rms}$ 42, is determined in RMS Operator 32. Assuming the two noise components, $N_1$ and $N_2$ are uncorrelated, their RMS values will add in the subtracted input signal 42 as the square root of the sum of the squares.

$$(S_1-S_2)_{rms} = (S-S)_{rms} + \sqrt{N_{1rms}^2 + N_{2rms}^2} = \sqrt{N_{1rms}^2 + N_{2rms}^2} \qquad \text{Equation 4}$$

Assuming the two noise components have approximately the same RMS values, i.e., $N_{1rms} = N_{2rms} = N_{rms}$, then the squared noise values are also the same:

$$N_{1rms}^2 = N_{2rms}^2 = N_{rms}^2 \qquad \text{Equation 5}$$

Substituting $N_{rms}^2$ 45 for $N_{1rms}^2$ and $N_{2rms}^2$ in Equation 4 gives:

$$(S_1-S_2)_{rms} = \sqrt{N_{rms}^2 + N_{rms}^2} = \sqrt{2N_{rms}^2} = 1.414 N_{rms} \qquad \text{Equation 6}$$

Solving Equation 6 for $N_{rms}$ 38:

$$N_{rms} = 0.707(S_1-S_2)_{rms} \qquad \text{Equation 7}$$

Accordingly, the SNR Estimator 27 scales the value of $(S_1-S_2)_{rms}$ 42 by 0.707 in Gain 33 to give the estimated RMS noise value, $N_{rms}$ 38:

Taking the RMS values of the two input signals in Equations 1 and 2 and assuming the desired signal, S, is uncorrelated with the noise, gives:

$$S_{1rms} = \sqrt{S_{rms}^2 + N_{1rms}^2} \qquad \text{Equation 8}$$

$$S_{2rms} = \sqrt{S_{rms}^2 + N_{2rms}^2} \qquad \text{Equation 9}$$

Since the two input signals, $S_1$ 25 and $S_2$ 26, are balanced, $S_{1rms} = S_{2rms}$ and either equation can be used to estimate $S_{rms}$ 40 the noise-free signal rms value. In this embodiment, the RMS value of balanced input signal $S_{2rms}$ 43 is determined in RMS Operator 35, but in other embodiments $S_{1rms}$ could be calculated and used.

From Equation 5, $N_{rms}^2 = N_{2rms}^2$. Substituting $N_{rms}^2$ for $N_{2rms}^2$ in Equation 9 gives:

$$S_{rms} = \sqrt{S_{rms}^2 + N_{rms}^2} \qquad \text{Equation 10}$$

Squaring both sides of Equation 10 gives:

$$S_{1rms}^2 = S_{rms}^2 + N_{rms}^2 \qquad \text{Equation 11}$$

The squared estimated noise RMS value, $N_{rms}^2$ 45, is determined from $N_{rms}$ 38 in Squarer 34 and the squared balanced signal RMS value, $S_{2rms}^2$ 44 is determined from $S_{2rms}$ 43 in Squarer 37.

Solving for the RMS value of $S_{rms}^2$ 46:

$$S_{rms}^2 = S_{2rms}^2 - N_{rms}^2 \qquad \text{Equation 12}$$

Subtracting $S_{2rms}^2$ 44 from $N_{rms}^2$ 45 is done in Subtractor 38 to give $S_{rms}^2$ 46. Taking the square root of Equation 12 gives $$S_{rms} = \sqrt{S_{rms}^2} = \sqrt{S_{2rms}^2 - N_{rms}^2} \qquad \text{Equation 13}$$

Taking the square root of the subtracted values, $S_{rms}^2$ 46, in Square Root Operator 39 gives the estimated RMS value of noise-free input signal, $S_{rms}$ 40.

The SNR can be calculated by taking the ratio of Equation 13 to Equation 7:

$$SNR = 20\log_{10}\left(\frac{S_{rms}}{N_{rms}}\right) dB \qquad \text{Equation 14}$$

To determine the SNR in dB 29, the estimated noise-free input RMS value, $S_{rms}$ 40, is divided by the estimated noise RMS value, $N_{rms}$ 38 in Divider 47. This result is converted to dB by taking 20 log in Convert Operator 48. This produces the estimated SNR in dB 29.

Figure 4:
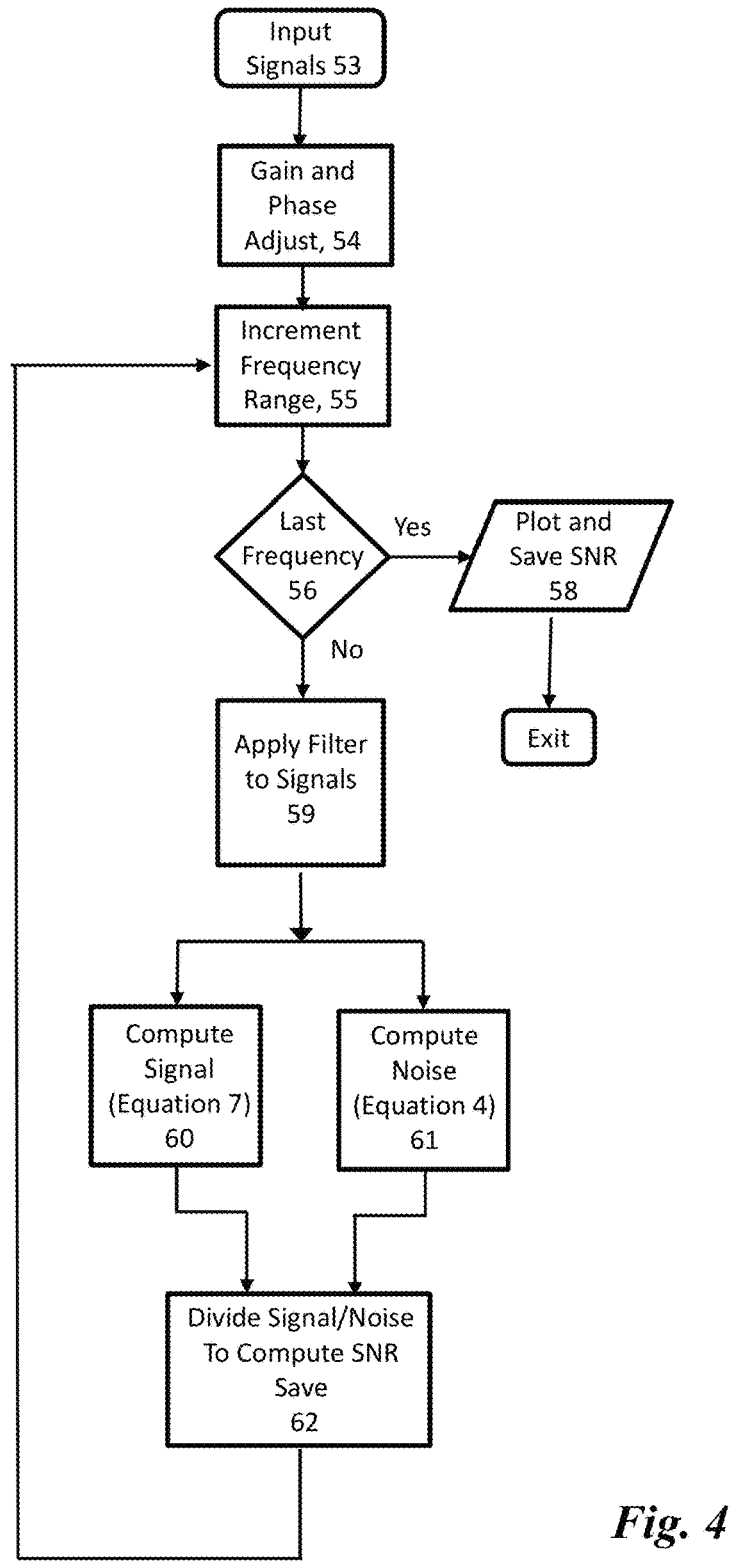
FIG. 4 is a flow diagram illustrating the implementation of the signal processing software shown in FIGS. 2 and 3.

FIG. 4 illustrates a flow diagram of the signal processing software 18. Input data 53 is delivered by the ADC 17 (FIG. 1). In step 54, the gain and phase shift operations 23 (FIG. 2) are applied to one of the input signals 54 to align the signals and balance gains as described above. In step 55, the frequency range is selected from a table of desired frequency ranges, and the software tests to see if the last desired frequency range has been analyzed in step 56. If the last desired frequency range has been analyzed, processing continues at step 58, which displays and saves the signal-to-noise ratio as a function of frequency. The program then exits. If the last frequency range has not been analyzed, processing continues in step 59 which implements the variable bandpass filters, 24 (FIG. 2). Step 59 first determines the Butterworth filter coefficients for desired frequency range then applies them to both signals. Step 60 determines the estimated noise free input signal RMS value, $S_{rms}$ 40 in accordance with Equation 13 using operations 35, 37, 38, and 39 (FIG. 3). Step 61 determines the estimated noise RMS value, $N_{rms}$ 38 in accordance with Equation 7 using operations 31, 32, and 33 (FIG. 3). In step 62, the estimated SNR 29 is determined from the estimated noise-free input signal RMS value, $S_{rms}$ 40 and estimated noise RMS value, $N_{rms}$ 38 in accordance with Equation 14 using operations 47 and 48 (FIG. 3).

The accuracy of the SNR estimation algorithm 27 was evaluated through simulation. A known amount of random Gaussian noise was added to two identical broadband signals to generate simulated signals $S_1$ 25 and $S_2$ 26. The SNR estimator 27 used these two signals to determine the estimated noise-free input signal RMS value, $S_{rms}$ 40, and the estimated noise RMS value, $N_{rms}$ 38.

Figure 5:
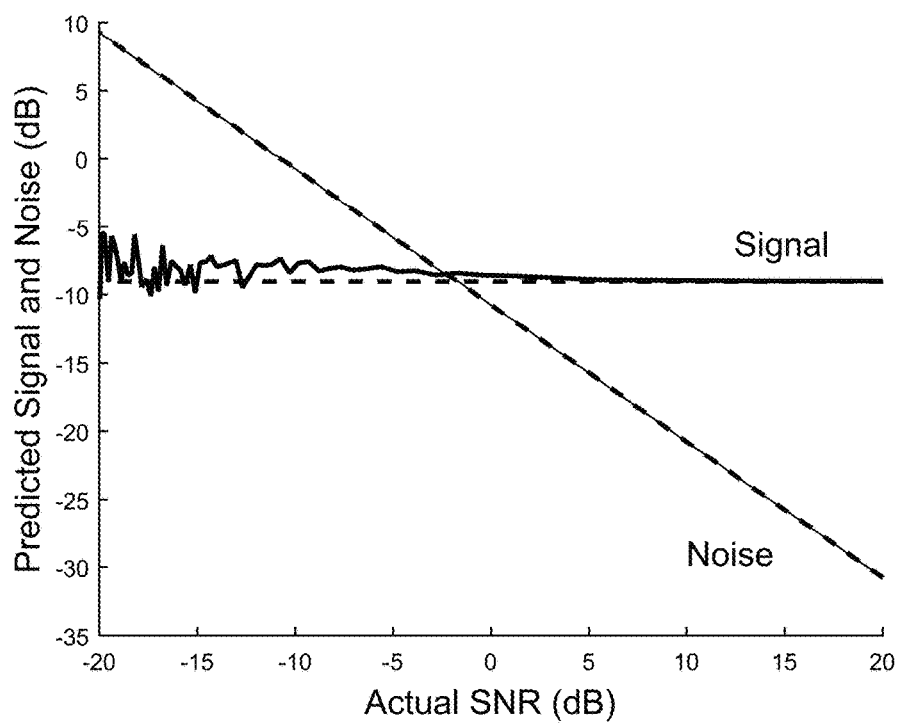
FIG. 5 is a graph illustrating the relationship between the estimated signal and estimated noise as a function of the actual signal-to-noise ratio.

In FIG. 5, a graph illustrates the relationship between the estimated signal and estimated noise as a function of the actual signal-to-noise ratio. The two estimated values are shown as a function of the actual SNR. The solid lines show the estimated values and the dashed lines the true values. The estimated noise RMS value, $N_{rms}$ 38, closely follows the true noise level for all SNR values; however, the estimated noise-free input signal RMS value, $S_{rms}$ 40, is higher than the true values and becomes erratic at SNR values less than approximately −12 dB. (An SNR of 0 dB means the signal and noise levels are equal.) The error in the estimated signal RMS value reflects the inability of the SNR estimator to accurately extract signal level when high noise levels are present (Note a SNR of −20 dB indicates that the noise level is 10 times the signal level.)

Figure 6:
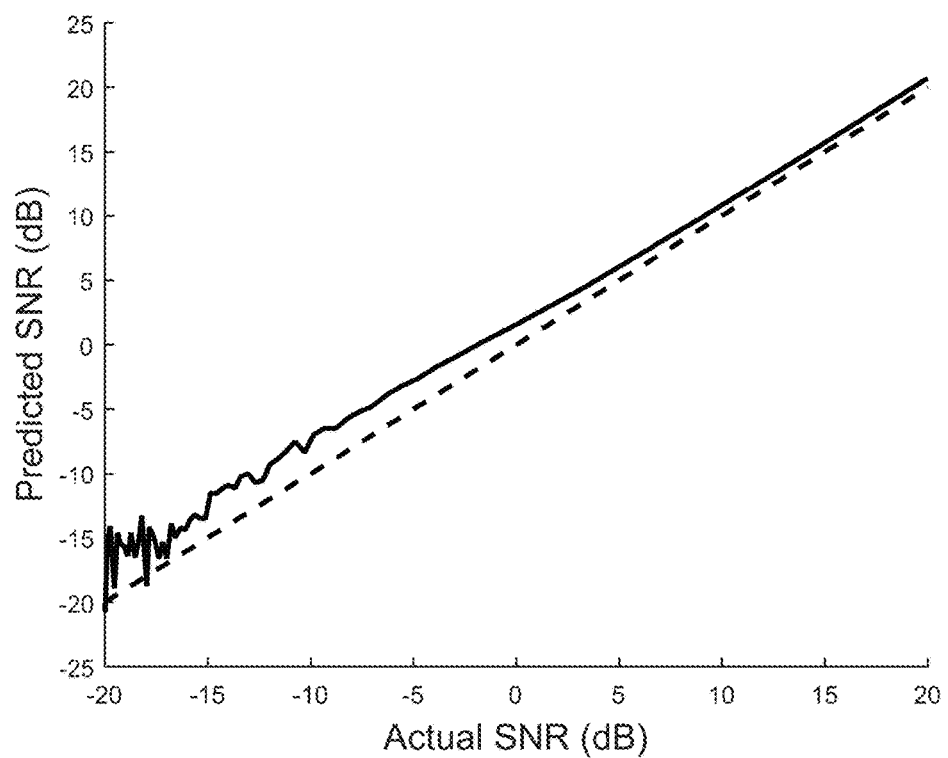
FIG. 6 is a graph illustrating the relationship between the estimated signal-to-noise ratio and the actual signal-to-noise ratio.

In FIG. 6 a graph illustrates the relationship between the estimated signal-to-noise ratio and the actual signal-to-noise ratio. The SNR predicted by the algorithm for the SNR Estimator 27 (FIG. 3) is shown as a function of true SNR in FIG. 6. Again the solid line is the estimated SNR 29 and the dashed line is the actual SNR. There is a small error between the actual and predicted SNR value.

Figure 7:
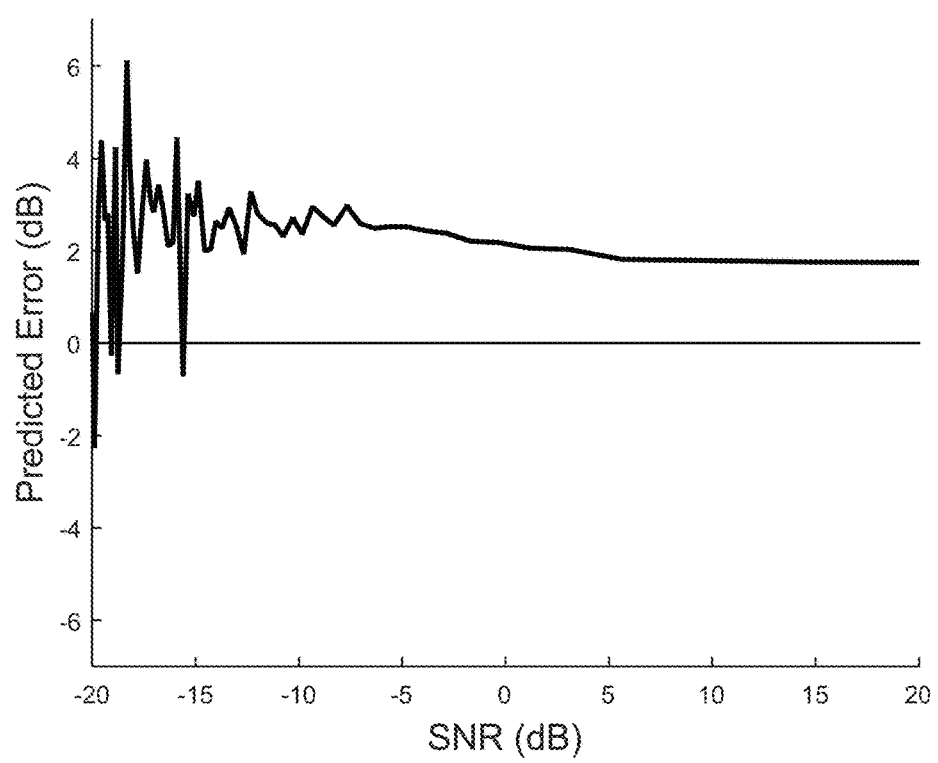
FIG. 7 is a graph showing the error in the signal-to-noise estimation as a function of the actual signal-to-noise ratio.

In FIG. 7 a graph illustrates the error in the signal-to-noise estimation as a function of the actual signal-to-noise ratio. This error is shown as the heavy solid line in FIG. 7. For values of SNR greater than approximately −10 dB, the error is fairly consistent and can be eliminated by simply subtracting the error curve from the estimated SNR. For SNR values below −10 dB, the error is approximately ±2 dB; however, in practice it is not necessary to accurately predict such low SNR values as they are well below useful values. For example, SNR values below 0 dB are thought to be too low to give reliable diagnostic information. Simulations have also shown that the two noise levels, $N_1$ and $N_2$ in Equations 2 and 3 do not have to be exactly the same. Specifically, an imbalance of ±25% produces a 1 dB error in the estimated SNR. Thus the signal processing means for predicting SNR from two signals, the SNR estimation algorithm 27, is shown to be sufficiently accurate for use in quantifying data quality.

While embodiments of the invention 10 have been described in detail above, the invention 10 is not limited to the specific embodiments described above, which should be considered as merely exemplary illustrations set forth for a clear understanding of the principles of the invention 10. Further variations, modifications, extensions, or equivalents of the invention 10 may be developed without departing from the scope of the invention 10. It is therefore intended that the invention 10 not be limited to the particular embodiments disclosed as the best mode contemplated for carrying out this invention, but that the invention 10 will include all the embodiments falling within the scope of the appended claims.

What is claimed is:

1. A computer implemented cardiac signal processing system, the system comprising:
    a dual-signal cardiac acoustic detector outputting dual cardiac analog acoustic signals produced by a single acoustic stimulus;
    a dual analog amplifier receiving analog acoustic signals from said cardiac acoustic detector;
    an analog-to-digital converter configured to receive analog output signals from said analog amplifier;
    an output device;
    a computing device configured to receive digital output signals from said analog-to-digital converter;
    and
    computer executable instructions executing on said computing device configured to:
    generate balanced digital signals by adjusting said digital output signals to have equal amplitudes and equal phase shifts;
    compute a subtracted digital signal by subtracting said balanced digital signals;
    compute an RMS value of said subtracted digital signal;
    scale said RMS value of said subtracted digital signal to generate an estimated noise RMS value of said balanced digital signals;
    square said estimated noise RMS value to produce a squared estimated noise RMS value;
    compute a balanced signal RMS value from either of said balanced digital signals;
    square said balanced signal RMS value to generate a squared balanced signal RMS value;
    subtract said squared estimated noise RMS value from said squared balanced signal RMS value to produce an estimated squared noise-free balanced digital signal RMS value;

compute a square root of said estimated squared noise-free balanced digital signal RMS value to produce an estimated noise-free balanced digital signal RMS value;

divide said estimated noise-free balanced digital signal RMS value by said estimated noise RMS value to compute an estimated signal-to-noise ratio for said balanced digital signals;

display said estimated signal-to-noise ratio on said output device;

whereby said output device includes a user interface for visual representation of said estimated signal-to-noise ratio of said cardiac analog acoustic signals; whereby the quality of said cardiac analog acoustic signals are quantitatively described by said estimated signal-to-noise ratio.

2. The system of claim 1, further comprising computer executable instructions executing on said computing device configured to:

compute RMS values of said digital output signals;

compute RMS values of a difference of said digital output signals.

3. The system of claim 1, wherein said signal-to-noise ratio is measured in decibels.

4. The system of claim 1, further comprising computer executable instructions executing on said computing device configured to:

produce band-limited digital output signals by initially band-limiting said digital output signals using a digital filter bank tuned to frequencies within a frequency range of said digital output signals;

whereby said estimated signal-to-noise ratio can be determined as a function of signal frequency.

5. The system of claim 4, further comprising:

a user interface configured within said output device;

displaying graphically at said user interface said signal-to-noise ratio as a function of frequency.

6. The system of claim 1, further comprising computer executable instructions executing on said computing device configured to generate aligned cardiac acoustic signals by first aligning said digital output signals using a maximum cross-correlation.

7. The system of claim 6, further including computer executable instructions executing on said computing device configured to combine said aligned cardiac acoustic signals to produce an improved signal-to-noise ratio in a resultant combined signal.

8. The system of claim 1, wherein computer executable instructions executing on said computing device are configured to normalize said digital output signals to have the same RMS values to compensate for any imbalance in said digital output signals.

9. The system of claim 1, further including computer executable instructions executing on said computing device configured to:

deliver to said output device an estimated noise-free balanced digital signal RMS value;

deliver to said output device an estimated noise RMS value.

10. A method for cardiac signal processing, the method comprising:

outputting from a dual-signal cardiac acoustic detector dual cardiac analog acoustic signals produced by a single acoustic stimulus;

receiving at a dual analog amplifier analog acoustic signals from said cardiac acoustic detector;

receiving at an analog-to-digital converter analog output signals from said analog amplifier;

outputting digital output signals from said analog-to-digital converter;

generating balanced digital signals by adjusting said digital output signals to have equal amplitudes and equal phase shifts;

computing a subtracted digital signal by subtracting said balanced digital signals;

computing an RMS value of said subtracted digital signal;

scaling said RMS value of said subtracted digital signal to generate an estimated noise RMS value of said balanced digital signals;

squaring said estimated noise RMS value to produce a squared estimated noise RMS value;

computing a balanced signal RMS value from either of said balanced digital signals;

squaring said balanced signal RMS value to generate a squared balanced signal RMS value;

subtracting said squared estimated noise RMS value from said squared balanced signal RMS value to produce an estimated squared noise-free balanced digital signal RMS value;

computing a square root of said estimated squared noise-free balanced digital signal RMS value to produce an estimated noise-free balanced digital signal RMS value;

dividing said estimated noise-free balanced digital signal RMS value by said estimated noise RMS value to compute an estimated signal-to-noise ratio for said balanced digital signals;

displaying said signal-to-noise ratio on an output device;

whereby said output device includes a user interface for visual representation of said estimated signal-to-noise ratio of said cardiac analog acoustic signals; whereby the quality of said cardiac analog acoustic signals are quantitatively described by said estimated signal-to-noise ratio.

11. The method of claim 10, further including the steps of:

computing RMS values of said digital output signals;

computing RMS values of a difference of said digital output signals.

12. The method of claim 10, wherein the step of computing an estimated signal-to-noise ratio further includes computing an estimated signal-to-noise ratio in decibels.

13. The method of claim 10, further including the steps of:

producing band-limited digital output signals by initially band-limiting said digital output signals using a digital filter bank tuned to frequencies within a frequency range of said digital output signals;

whereby said estimated signal-to-noise ratio can be determined as a function of signal frequency.

14. The method of claim 13, further including the steps of:

providing a user interface configured within said output device;

displaying graphically at said user interface said signal-to-noise ratio as a function of frequency.

15. The method of claim 10, further including the step of:

generating aligned cardiac acoustic signals by first aligning said digital output signals using a maximum cross-correlation.

16. The method of claim 15, further including the step of:

combining said aligned cardiac acoustic signals to produce an improved signal-to-noise ratio in a resultant combined signal.

17. The method of claim 10, further including the step of:
normalizing said digital output signals to have the same RMS values to compensate for any imbalance in said digital output signals.

18. The method of claim 10, further including the steps of:
delivering to said output device an estimated noise-free balanced digital signal RMS value;
delivering to said output device an estimated noise RMS value.

* * * * *